US008808393B2

(12) United States Patent
Bergande

(10) Patent No.: US 8,808,393 B2
(45) Date of Patent: Aug. 19, 2014

(54) LEG PROSTHESIS

(75) Inventor: Stefan Bergande, Beedenbostel (DE)

(73) Assignee: Prolutions GmbH, Celle (DE)

( * ) Notice: Subject to any disclaimer, the term of this patent is extended or adjusted under 35 U.S.C. 154(b) by 85 days.

(21) Appl. No.: 13/419,113

(22) Filed: Mar. 13, 2012

(65) Prior Publication Data
US 2012/0239163 A1 Sep. 20, 2012

(30) Foreign Application Priority Data

Mar. 15, 2011 (DE) .......................... 10 2011 013 970

(51) Int. Cl.
*A61F 2/80* (2006.01)
*A61F 2/76* (2006.01)
*A61F 2/78* (2006.01)
*A61F 2/50* (2006.01)

(52) U.S. Cl.
CPC ........... *A61F 2/76* (2013.01); *A61F 2002/5083* (2013.01); *A61F 2/78* (2013.01); *A61F 2/80* (2013.01); *A61F 2002/5018* (2013.01)
USPC ............................................. 623/33; 623/38

(58) Field of Classification Search
CPC ................ A61F 2002/5018; A61F 2002/5021; A61F 2002/5023; A61F 2002/5083
USPC ..................................................... 623/33, 38
See application file for complete search history.

(56) References Cited

U.S. PATENT DOCUMENTS

| 5,507,837 A | 4/1996 | Laghi |
| 5,888,234 A | 3/1999 | Littig |
| 6,991,658 B2 | 1/2006 | Slemker et al. |
| 7,083,654 B2 | 8/2006 | Helenberger et al. |
| 2002/0193887 A1 | 12/2002 | Swanson |
| 2011/0015761 A1 | 1/2011 | Celebi et al. |

FOREIGN PATENT DOCUMENTS

| DE | 102006021064 A1 | 11/2007 | |
| RU | 2 475 214 C2 * | 11/2012 | ................ A61F 2/76 |
| WO | WO 98/43559 A1 * | 10/1998 | ................ A61F 2/76 |

* cited by examiner

*Primary Examiner* — David H Willse
(74) *Attorney, Agent, or Firm* — Cohen & Hildebrand, PLLC

(57) ABSTRACT

A leg prosthesis wherein the prosthesis shaft and the transtibial part are connected by a prosthesis shaft adapter. The prosthesis shaft adapter is constructed as a compact one-part component with a liner (sleeve as inner prosthesis shaft adapter) of the amputation stump and with a rearward extension for the prosthesis receptacle connection. The prosthesis shaft adapter is designed such that, in addition to the rearward extension of 1 cm to 10 cm, the prosthesis receptacle connection is also angled and laterally offset. Advantageously, the leg prosthesis according to the invention has a relatively low weight due to the prosthesis shaft adapter as a connecting element. The leg prosthesis operates absolutely safely and can be efficiently produced. The fabrication of a leg prosthesis with an individual biomechanical fit to the patient is significantly facilitated, which also results in fewer faulty prostheses.

7 Claims, 4 Drawing Sheets

LEG PROSTHESIS

Figure 1:
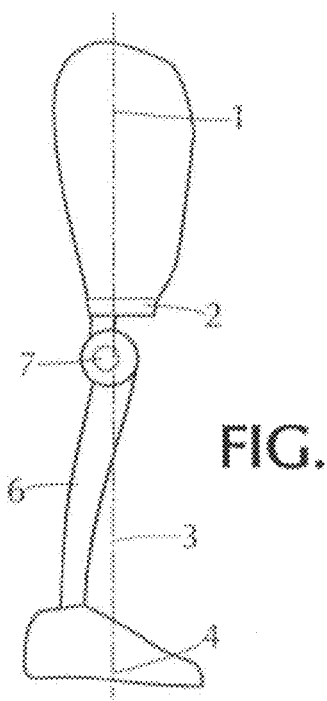

BACKGROUND OF THE INVENTION (1) Field of the Invention

The invention relates to a leg prosthesis, consisting of a prosthesis shaft with a prosthesis shaft adapter non-releasably integrated therein and a transtibial part with a foot and a knee joint part or a transtibial part with a foot, wherein the prosthesis shaft and the transtibial part are releasably connected with each other by way of the prosthesis shaft adapter.

(2) Description of Related Art

Leg prostheses and prosthesis shaft adapters producing a suitable mechanical connection between the prosthesis shaft and the transtibial part of a leg prosthesis are known. Frequently, a so-called inner shaft, or liner, made of a soft flexible material, for example silicone, is used in the hollow space of the prosthesis shaft for direct skin contact and as adhesion promoter on the skin. The lower closed end of the liner has a metal pin which is connected to the liner over a large area, wherein the pin can be locked with the liner through an opening in the lower prosthesis part and fixed in this position.

For applying the liner on the amputation stump, the liner is rolled up on the amputation stump and then inserted into the actual prosthesis shaft and connected and locked by the metal pin with an adapter in or on the prosthesis shaft for securing the liner on the knee joint component.

For removing the liner, the lock is released again and the amputation stump with the liner is pulled out of the prosthesis shaft and rolled down.

For realizing this mechanical process, at least one additional adapter is required on the alignment line between the hip joint and the midfoot for vertical biostatic force flux equalization. In practice, however, several adapters are frequently required for shifting the coupling location or the connection location to the knee joint of the transtibial part back.

Disadvantageously, several adapters may be required for shifting or returning the connection between the prosthesis shaft and the knee joint of the transtibial part due to the size of the patient and the length of the amputation stump. However, the overall height is determined by the patient and is frequently not adequate for the system to enable a proper fit. Alternatively, very expensive custom-built designs need to be considered.

When using several adapters, their relatively high weight and an increased accident risk due to the large number of components and the costs for these components are disadvantageous (U.S. Pat. No. 5,888,234; U.S. Pat. No. 5,507,837; U.S. Pat. No. 7,083,654; U.S. 2011-0015761 A1).

BRIEF SUMMARY OF THE INVENTION

It is an object of the invention to provide a leg prosthesis with a prosthesis adapter having minimal height, minimal weight and a small number of components that can be easily handled and operates safely, which has a structure that can be adapted and used universally and individually. Trained personnel producing prostheses should be able to efficiently, easily and inexpensively fabricate the prosthesis adapter.

According to the invention, this object is attained with the recited claims.

The basic structure of the prosthesis shaft adapter of the leg prosthesis for forming a custom-fit connection between the prosthesis shaft and the transtibial part is hereby formed as a compact one-piece component. The prosthesis shaft adapter is, on one hand, designed with an integrated amputation stump receiving cup with or without connection mechanism and locking mechanism for the liner (sleeve as inner prosthesis adapter), such as a Velcro tape lock, a drawstring or safety pin lock, or a connection of the amputation stump with a vacuum pump and vacuum control valves on the amputation stump.

On the other hand, the prosthesis shaft adapter is constructed with an integrated rearward extension A, i.e. rearward relative to the walk direction line, to provide a spacing from the amputation stump cup and a prosthesis receptacle connection for the transtibial part or a screwable knee joint assembly.

The prosthesis shaft adapter is herein dimensioned such that the rearward extension A with spacing between the centerline (center) of the amputation stump cup in the prosthesis shaft adapter and center of the prosthesis receptacle connection can be 1 cm to 10 cm. The prosthesis receptacle connection is hereby designed such that the centerline of the attached transtibial part 6 or of the knee joint assembly extends in relation to the centerline of the cup and an imaginary vertical alignment line 3 from the hip joint to the midfoot at an acute angle $\alpha$ from 5° to 20°.

In another embodiment, the prosthesis receptacle connection of the rearward extension A may also be offset to the side, by an offset B, from the walk direction line, so that in addition to the rearward extension A also a sideways displacement of the prosthesis receptacle connection 10 can be implemented with the offset B to a walk direction line parallel to the walk direction line.

The prosthesis shaft adapter is herein dimensioned such that the rearward extension A with spacing between the center of the amputation stump cup in the prosthesis shaft adapter and the center of the prosthesis receptacle connection 10 may be 1 cm to 10 cm, with the lateral offset B potentially reaching ±6 cm.

The prosthesis receptacle connection for attachment of the transtibial part or the knee joint assembly may be a flange connection with a flange, an axial screw connection with a thread, a bayonet connection or a non-releasable connection.

Advantageously, the leg prosthesis according to the invention has a prosthesis shaft adapter of significantly less weight than other comparable prosthesis shaft adapters and consists of only a single compact component. The leg prosthesis can be optimally biokinetically fitted to the patients with the prosthesis shaft adapter, in particular also due to the lateral offset in relation to the walk line.

The prosthesis shaft adapter operates absolutely safely and maintenance-free by minimizing components, such as screws, etc., and can be produced efficiently. An orthopedic technician can much more easily fabricate these leg prostheses with an excellent individual biomechanical fit to the patient, which also helps to prevent a faulty fabrication.

The invention will now be described with reference to two exemplary embodiments.

BRIEF DESCRIPTION OF THE SEVERAL VIEWS OF THE DRAWING(S)

The appended drawing shows in

Figure 2:
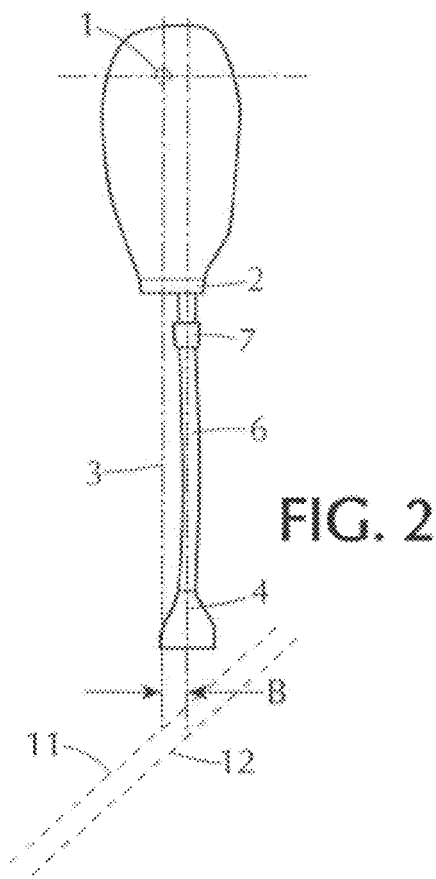
Figure 3:
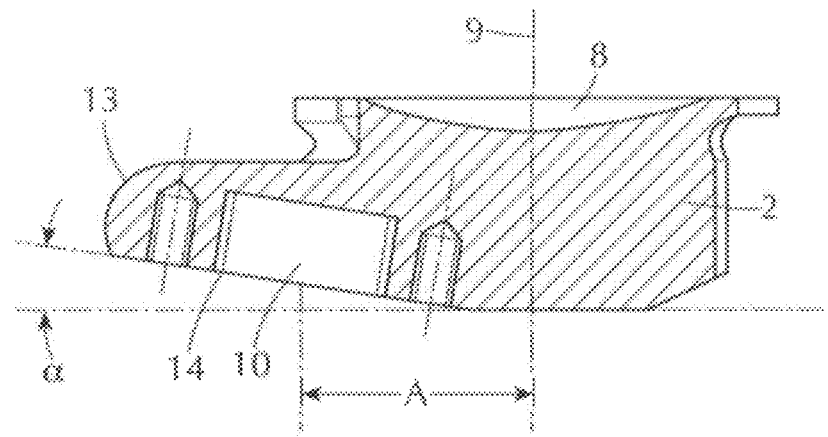
Figure 4:
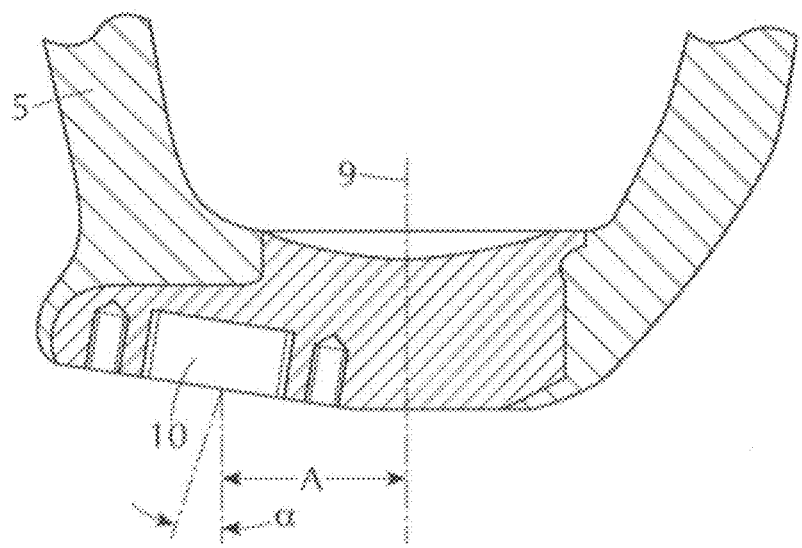
Figure 5:
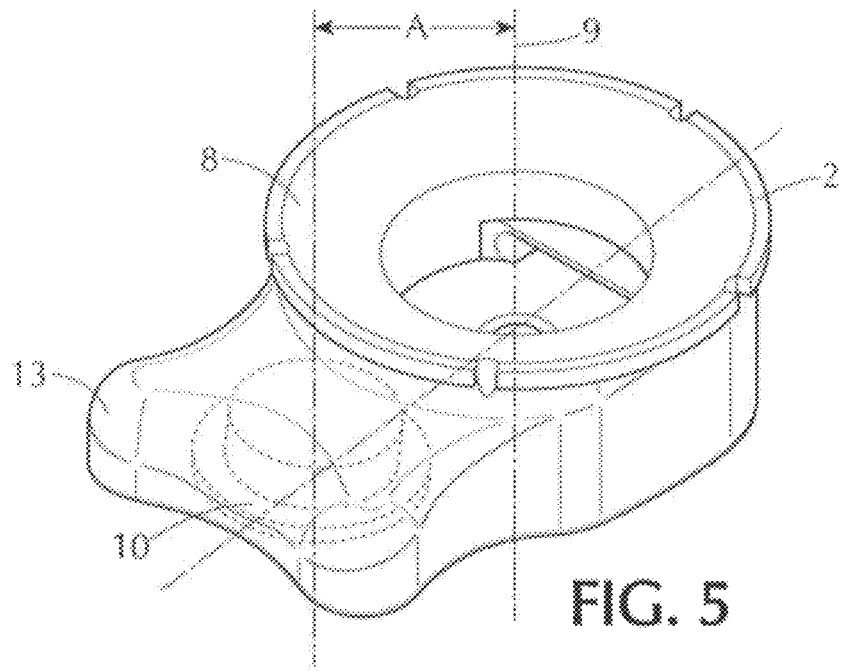
Figure 6:
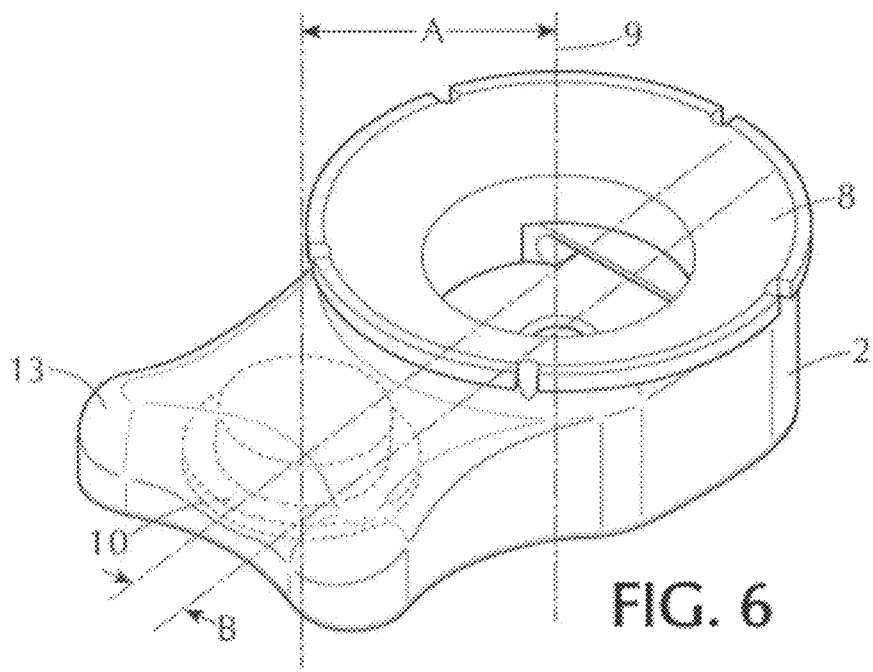
Figure 7:
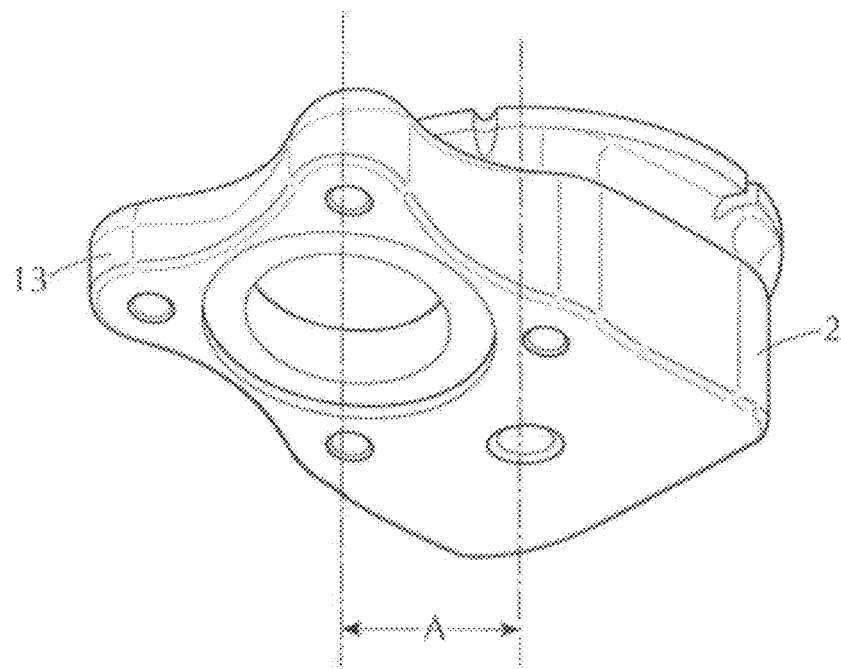

FIG. 1 a leg prosthesis with a prosthesis shaft, a prosthesis shaft adapter assembly and a transtibial part in a side view, FIG. 2 a leg prosthesis with a prosthesis shaft, a prosthesis shaft adapter assembly and a transtibial part in a front view, FIG. 3 a prosthesis shaft adapter in cross-section, FIG. 4 a prosthesis shaft adapter formed in the prosthesis shaft in cross-section, FIG. 5 a prosthesis shaft adapter in a perspective top view, FIG. 6 a prosthesis shaft adapter with a lateral offset, and FIG. 7 a schematic diagram of a prosthesis shaft adapter in a perspective bottom view.

DETAILED DESCRIPTION OF THE INVENTION

In one embodiment, the basic structure of the prosthesis shaft adapter 2 of the leg prosthesis for forming a custom-fit connection between the prosthesis shaft 5 and the transtibial part 6 is hereby formed as a compact one-piece component. The prosthesis shaft adapter 2 is, on one hand, designed with an integrated amputation stump receiving cup 8 with or without connection mechanism and locking mechanism for the liner (sleeve as inner prosthesis adapter), such as a Velcro tape lock, a drawstring or safety pin lock, or a connection of the amputation stump with a vacuum pump and vacuum control valves on the amputation stump.

On the other hand, the prosthesis shaft adapter 2 is constructed with an integrated rearward extension A, i.e. rearward relative to the walk direction line, to provide a spacing from the amputation stump cup 8 and a prosthesis receptacle connection 10 for the transtibial part 6 or a screwable knee joint assembly 7.

The prosthesis shaft adapter 2 is herein dimensioned such that the rearward extension A with spacing between the centerline 9 (center) of the amputation stump cup 8 in the prosthesis shaft adapter 2 and center of the prosthesis receptacle connection 10 can be 1 cm to 10 cm.

The prosthesis receptacle connection 10 is hereby designed such that the centerline of the attached transtibial part 6 or of the knee joint assembly 7 extends in relation to the centerline 9 of the cup and an imaginary vertical alignment line 3 from the hip joint 1 to the midfoot 4 at an acute angle α from 5° to 20°.

In another embodiment, the prosthesis receptacle connection 10 of the rearward extension A may also be offset to the side, by an offset B, from the walk direction line 12, so that in addition to the rearward extension A also a sideways displacement of the prosthesis receptacle connection 10 can be implemented with the offset B to a offset walk direction line 11 parallel to the walk direction line 12.

The prosthesis shaft adapter 2 is herein dimensioned such that the rearward extension A with spacing between the center 9 of the amputation stump cup 8 in the prosthesis shaft adapter 2 and the center of the prosthesis receptacle connection 10 may be 1 cm to 10 cm, with the lateral offset B potentially reaching ±6 cm.

The prosthesis receptacle connection 10 for attachment of the transtibial part 6 or the knee joint assembly 7 may be a flange connection with the flange 13, an axial screw connection with a thread 14, a bayonet connection or a non-releasable connection.

Advantageously, the leg prosthesis according to the invention has a prosthesis shaft adapter of significantly less weight than other comparable prosthesis shaft adapters and consists of only a single compact component. The leg prosthesis can be optimally biokinetically fitted to the patients with the prosthesis shaft adapter, in particular also due to the lateral offset in relation to the walk line.

The prosthesis shaft adapter operates absolutely safely and maintenance-free by minimizing components, such as screws, etc., and can be produced efficiently. An orthopedic technician can much more easily fabricate these leg prostheses with an excellent individual biomechanical fit to the patient, which also helps to prevent a faulty fabrication.

EXAMPLE 1

For fabricating an individual leg prosthesis for a femoral amputation stump, the orthopedic technician initially measures and determines according to the alignment line 3 from the hip joint 1 to the midfoot 4 a prosthesis shaft adapter 2 according to the invention in accordance with biomechanical criteria with respect to a measured required rearward extension A of 5 cm on a walk direction line 12 without a lateral offset B and an angle of its prosthesis receptacle connection 10 of 9°, and selects a flange connection with flange fitting 14 as the prosthesis receptacle connection 10.

The prosthesis shaft adapter 2 determined in this manner is then formed fixedly and non-releasably in the lower part of the prosthesis shaft 5 such that the prosthesis receptacle connection 10 for the transtibial part 6 is exposed and accessible for its installation or the installation of its knee joint assembly 7. The installation is then performed in a conventional manner. With the rearward extension A and the angle of the transtibial receptacle connection 10, a leg prosthesis according to biomechanical criteria can be optimally realized.

EXAMPLE 2

For fabricating an individual leg prosthesis for a femoral amputation stump, the orthopedic technician initially measures and determines a prosthesis shaft adapter 2 according to the invention with respect to a measured required rearward extension A of 7 cm and an angle of its prosthesis receptacle connection 10 of 15° and a lateral offset B of 4 cm in accordance with biomechanical criteria, and selects a screw connection with an interior thread 14 as the connection between the prosthesis shaft adapter 2 and the transtibial part 6.

The prosthesis shaft adapter 2 determined in this manner is then formed fixedly and non-releasably in the lower part of the prosthesis shaft 5 such that the prosthesis receptacle connection 10 for the transtibial part 6 is exposed and accessible for its installation or the installation of its knee joint assembly 7.

The installation is then performed in a conventional manner. With the rearward extension A and the angle of the transtibial receptacle connection 10 and the lateral offset B, a leg prosthesis according to biomechanical criteria can be optimally realized.

The invention claimed is:

1. A leg prosthesis, comprising
a prosthesis shaft (5) including an integrated prosthesis shaft adapter (2),
transtibial part (6) with a foot or with a foot and a knee joint assembly (7),
wherein the prosthesis shaft adapter (2) is constructed as a compact monolithic one-part component for establishing a fitted connection between the prosthesis shaft (5) and the transtibial part (6), and including an integrated amputation stump receiving cup (8) with an integrated rearward extension (A), relative to the walk direction, on a walk line (12) of the walk direction or on a walk line (11) which is parallel thereto with a lateral offset (B),
wherein the effective rearward extension (A) from a center line (9) of the amputation stump receiving cup (8), at a right angle to the amputation stump cup surface, to the center of a prosthesis receptacle connection (10) for the transtibial part (6) is dimensioned from 1 cm to 10 cm, and
wherein the prosthesis receptacle connection (10) for the transtibial part (6) is constructed such that the centerline of the attached transtibial part (6), with or without a knee joint assembly (7) screwed thereto, extends with respect to the cup centerline (9) and an imaginary vertical alignment line (3) from the hip joint (1) to the midfoot (4) at an acute angle α from 5° to 20° thereto.

2. The leg prosthesis according to claim 1, wherein with the lateral offset of the assembly of the transtibial part (6) on the parallel walk line (11), the prosthesis receptacle connection (10) on the prosthesis shaft adapter (2) is arranged with the offset (B) of up to ±6 cm.

3. The leg prosthesis according to claim 1, wherein the prosthesis receptacle connection (10) is a flange connection with flange (13) or an axial screw connection with thread (14) or a bayonet connection or a non-releasable connection.

4. The leg prosthesis according to claim 1, wherein the prosthesis shaft adapter (2) is disposed entirely within an opening defined in the prosthesis shaft (5).

5. The leg prosthesis according to claim 4, wherein the prosthesis shaft adapter (2) does not extend in a direction toward the transtibial part (6) beyond the prosthesis shaft (5).

6. The leg prosthesis according to claim 1, wherein the amputation stump receiving cup (8) is a recess defined in a top surface of the prosthesis shaft adapter (2).

7. The leg prosthesis according to claim 1, wherein the prosthesis shaft adapter (2) is non-releasably integrated in a lower part of the prosthesis shaft (5).

* * * * *